United States Patent [19]
Ladisch et al.

[11] Patent Number: 5,624,553
[45] Date of Patent: Apr. 29, 1997

[54] DEVICE FOR PACKING CHROMATOGRAPHIC STATIONARY PHASES

[75] Inventors: Michael Ladisch; Kent Hamaker; Richard Hendrickson; Mark Brewer, all of West Lafayette, Ind.

[73] Assignee: Purdue Research Foundation, West Lafayette, Ind.

[21] Appl. No.: 553,749

[22] Filed: Oct. 23, 1995

Related U.S. Application Data

[62] Division of Ser. No. 260,021, Jun. 15, 1994.

[51] Int. Cl.$^6$ ................................................. B01D 15/08
[52] U.S. Cl. ..................... 210/198.2; 210/232; 210/237; 210/541; 210/656
[58] Field of Search ................................... 210/635, 659, 210/656, 198.2, 232, 236, 237, 238, 249, 541; 95/88; 96/101, 149

[56] References Cited

U.S. PATENT DOCUMENTS

| | | | |
|---|---|---|---|
| 1,777,970 | 10/1930 | Hartmann | 210/198.2 |
| 4,986,909 | 1/1991 | Rai | 210/198.2 |
| 5,017,290 | 5/1991 | Namikoshi | 210/198.2 |
| 5,032,277 | 7/1991 | Okamoto | 210/198.2 |
| 5,041,226 | 8/1991 | Shibata | 210/198.2 |
| 5,059,328 | 10/1991 | Shibata | 210/198.2 |
| 5,108,596 | 4/1992 | Ookuma | 210/198.2 |
| 5,135,650 | 8/1992 | Hjerten | 210/198.2 |
| 5,160,627 | 11/1992 | Cusslec | 210/198.2 |
| 5,334,310 | 8/1994 | Frechet | 210/198.2 |

FOREIGN PATENT DOCUMENTS

WO9007965  7/1990  WIPO .................. 210/198.2

OTHER PUBLICATIONS

Rowland, S.P., Roberts, E.J., and Wade, C.P., "Selective Accessibilities Of Hydroxyl Groups In The Microstructure Of Cotton Cellulose", *Textile Research J.*, vol. 39, pp. 530–542 (1969).

Soignet, D.M., Berni, R.J., and Benerito, R.R., "Comparison Of Properties Of Anion–Exchange Cottons In Fabric Form", *Textile Research J.*, vol. 36, pp. 978–989 (1966).

Roy, D. and Knoigsbert, W., "Chromatography Of Proteins And Peptides On Diethylaminoethyl Cellulose", *Methods In Enzymology*, vol. XXV, Enzyme Structure, Part B., Hirs, C.H.W. and Timasheff, S.N. Editors, Chapter 17, pp. 221–231.

Sober, H.A., Gutter, F.J., Wyckoff, M.M., and Peterson, E.A., "Chromatography Of Proteins. II. Fractionation Of Serum Protein On Anion–Exchange Cellulose", *J. Of The Amer. Chem. Soc.*, vol. 78, pp. 756–763 (1955).

Schubert, W.M. and Zahler, R.E., "Aromatic Electrophilic Substitution By Hydrogen. III. The Mechanism Of The Acid–Catalyzed Decarboxylation Of Aromatic Aldehydes $^{1,2}$", *J. Of The Amer. Chem. Soc.*, vol. 76, pp. 1711–1712 (1954).

(List continued on next page.)

*Primary Examiner*—Ernest G. Therkorn
*Attorney, Agent, or Firm*—Woodard, Emhardt, Naughton Moriarty & McNett

[57] ABSTRACT

Devices and methods for packing a chromatography column with a continuous stationary phase. The preferred device includes a brace member with an engagement surface. The brace member defines a thru-hole at a location so that a passageway defined through the column is aligned with the thru-hole of the brace member when a first end of the column is engaged with the engagement surface of the brace member. A funnel member engageable with an end of the column opposite the first end. The funnel member has converging walls configured to radially compress the continuous stationary phase for entry into the passageway of the column when the continuous stationary phase is pulled through the funnel member. The device includes a mechanism for applying mechanical force to pull the rolled continuous stationary phase through the funnel member wherein the stationary phase is radially compressed and enters the passageway of the column.

9 Claims, 6 Drawing Sheets

OTHER PUBLICATIONS

Tsuei, A.C.R. and Yang, V.C., "Ion–Exchange Hollow Fibers", *Amer. Chem. Soc.*, vol. 31, No. 1, pp. 238–239 (1990).

Kumar, A., "Enzymatic Finishing Of Lyocell Fabrics", *Book of Papers; 1994 International Conference & Exhibition*, Amer. Assoc. of Textile Chemists and Colorists (Abstract), Genencor International Inc., South San Francisco, California, p. 488 (1994).

Guthrie, J.D., and Bullock, A.L., "Ion Exchange Celluloses For Chromatographic Serparation", *Ind. Eng. Chem.*, vol. 52, pp. 935–937 (1960).

Hoffpauir, C.L. and Guthrie, J.D., "Ion–Exchange Characteristics Of Chemically Modified Cotton Fabrics", *Textile Res. J.*, vol. 20, pp. 617–620 (1950).

James, K. and Stanworth, D.R., "Studies On The Chromatography Of Human Serum Protein On Deithylamino–Ethyl (DEAE)—Cellulose I. The Effect Of The Chemical And Physical Nature Of The Exchanger", *J. Chromatogr.*, vol. 15, pp. 324–335 (1964).

Knight, C.S., "Some Fundamentals Of Ion–Exchange–Cellulose Design And Usage In Biochemistry", *Advances In chromatography*, vol. 4, Giddings, J.C. and Keller, R.A. (eds.), Marcel Dekker, Inc., New York, NY, pp. 61–110 (1967).

Peteson, E.Q. and Sober, H.A., "Chromatography Of Proteins. I. Cellulose Ion–Exchange Adsorbents", *J. Am. Chem. Soc.*, vol. 78, pp. 751–755 (1956).

Roberts, E.J., Bose, J.L. and Rowland, S.P., "Evidence For Two Types Of Accessible Surfaces In Fibrous Cotton", *Textile Res. J.*, vol. 42, pp. 217–221 (1972).

Yang, Y., Velayudhan, A., Ladisch, C.M. and Ladisch, M.R., "Protein Chromatography Using A Continuous Stationary Phase", *J. Chromatogr.*, vol. 598, pp. 169–180 (1992).

Yang, Y., Velayudhan, A., Ladisch, C.M. and Ladisch, M.R., "Liquid Chromatography Using Cellulosic Continuous Stationary Phases", *Biotechnology*, vol. 49, pp. 147–160 (1993).

DEVICE FOR PACKING CHROMATOGRAPHIC STATIONARY PHASES

This invention was made with Government support under Grant No. BCS 8912150, awarded by the National Science Foundation. The government has certain rights in the invention.

This application is a division of application Ser. No. 08/260,021, filed Jun. 15, 1994.

FIELD OF THE INVENTION

The present invention broadly concerns chromatography, particularly, stationary phases for use in chromatography. More specifically, the invention concerns devices and methods for packing chromatography columns with continuous stationary phases.

BACKGROUND OF THE INVENTION

Chromatography is one of the most widely used analytical techniques in biotechnology. Currently, separation costs account for well over 40% of the production expenses associated with the manufacture of proteins and other biotechnology products. Key objectives towards managing these costs include reducing the number or complexity of production steps and labor costs.

Particulate supports are the most commonly used materials for chromatographic stationary phases. However, these materials are inefficient for large scale operations which require speed, scale up and ease of clean operation. On the other hand, continuous stationary phases formed of fabric (i.e. a textile structure composed of mechanically interlocked fibers or filaments) provide many advantages compared to discrete spherical or granular packing materials, including: mechanical stability at extremely high eluent linear velocities, wide availability of a range of defined surface chemistries in large quantities, and constant plate height at high linear velocities, thereby making scale-up and operation over a wide range of conditions relatively independent of flow rate. Furthermore, the fabric, when packed tightly in column, retains the advantage of low pressure drops, which is difficult to achieve with particulate forms of the same materials.

Continuous stationary phases have further advantages over loose packing materials, including, very fast flow rates, direct scale-up, and clean columns. These advantages are not currently found in preparative and commercial scale chromatography using particulate cellulosic stationary phases.

In spite of these advantages, columns having continuous phases of fabric are difficult to pack with sufficient density and reproducibility. A need thus exists for devices and methods which provide reproducible, dense packing of a large number of columns at reasonable expense. The present invention addresses this need.

SUMMARY OF THE INVENTION

In accordance with the invention, devices and methods are provided for packing a chromatography column with a continuous stationary phase. Briefly mentioning one aspect of the invention, such a device includes a brace member having an engagement surface for engaging a column to be packed. The brace member also defines a hole extending completely through the brace member (hereinafter "thru-hole") at a location so that the passageway defined through the column is aligned with the thru-hole of the brace member when an end of the column is engaged with the engagement surface. The device also includes a funnel member engageable with an end of the column opposite the engaged end, wherein the funnel member has converging walls configured to radially compress the continuous stationary phase for entry into the passageway of the column when the continuous stationary phase is pulled through the funnel member. A mechanism is also provided for applying mechanical force to pull the rolled continuous stationary phase through the funnel member wherein the stationary phase is radially compressed upon entering the passageway of the column.

Another preferred embodiment of the invention provides a process for packing a chromatography column with a continuous stationary phase. The inventive process comprises the step of providing a continuous stationary phase and a column having a passageway therethrough, wherein the passageway is sized to receive the continuous stationary phase upon radial compression of the continuous stationary phase. A funnel member is provided having converging walls configured to radially compress the continuous stationary phase upon passage of the stationary phase through the funnel member. In accordance with the invention, the continuous stationary phase is positioned within the passageway of the column with applied mechanical force, wherein the positioning includes passage of the continuous stationary phase through the funnel member so as to radially compress the continuous stationary phase, as it is being pulled or packed into the column.

One object of the invention is to provide a device which reliably and efficiently packs continuous stationary phase material into chromatography columns.

Another object of the present invention is to provide methods for quickly and reproducibly packing continuous stationary phase material into chromatography columns.

Additional objects, features and advantages of the invention will be apparent from the following description.

DESCRIPTION OF THE PREFERRED EMBODIMENT

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides devices and methods for packing a chromatography column, such as a liquid or gas chromotagraphy column, with a continuous stationary phase. The invention thus enables the exploitation of the advantages of continuous stationary phase materials in large scale operations. Continuous stationary phase materials are excellent sorbents and can be effectively derivatized to improve their sorbent properties. For example, continuous stationary phases formed with materials such as cotton and other cellulosic materials have proven highly effective in the separation of proteins and other substances.

Figure 1:
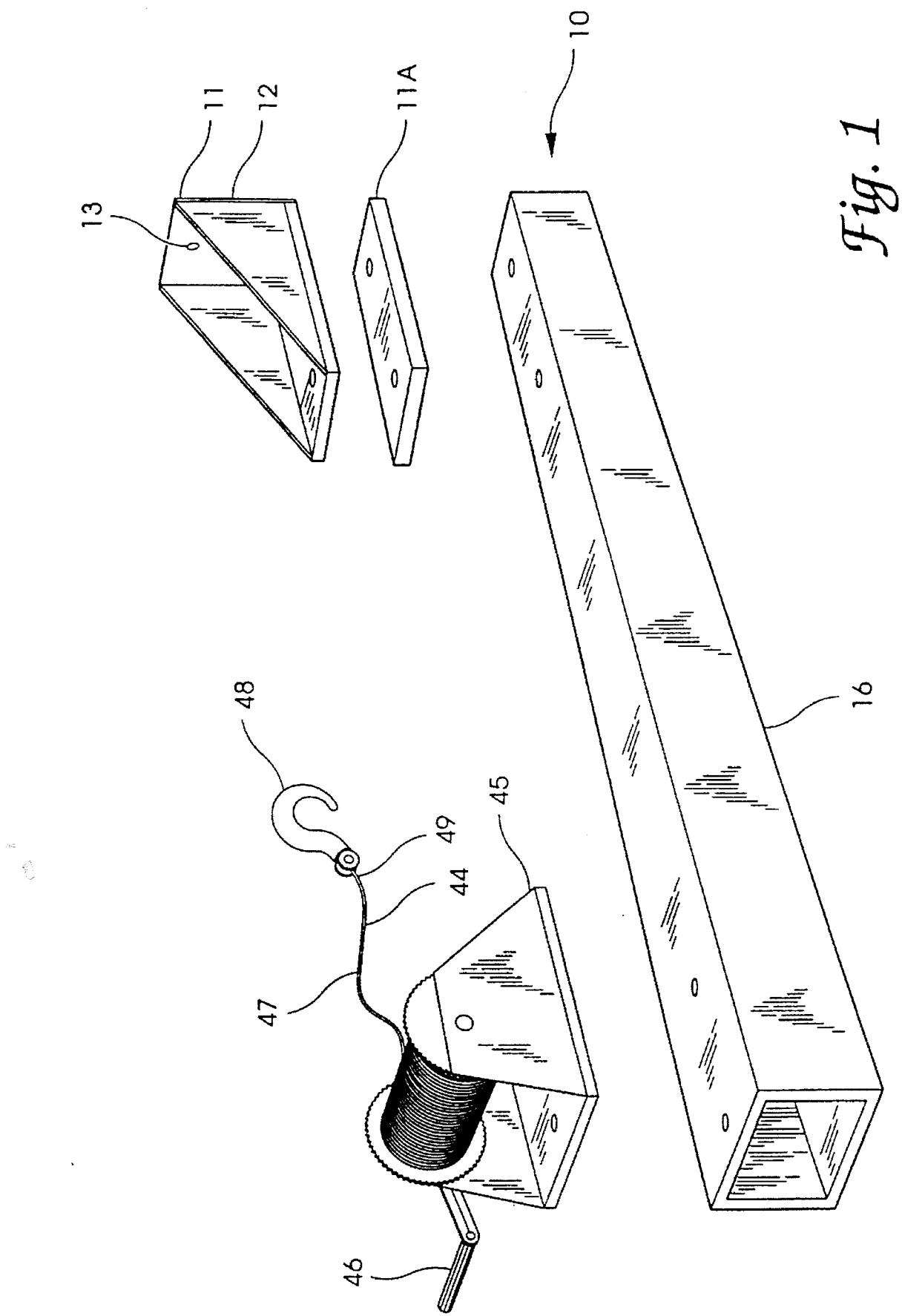
FIG. 1 is an exploded perspective view of a device of the present invention.
Figure 2:
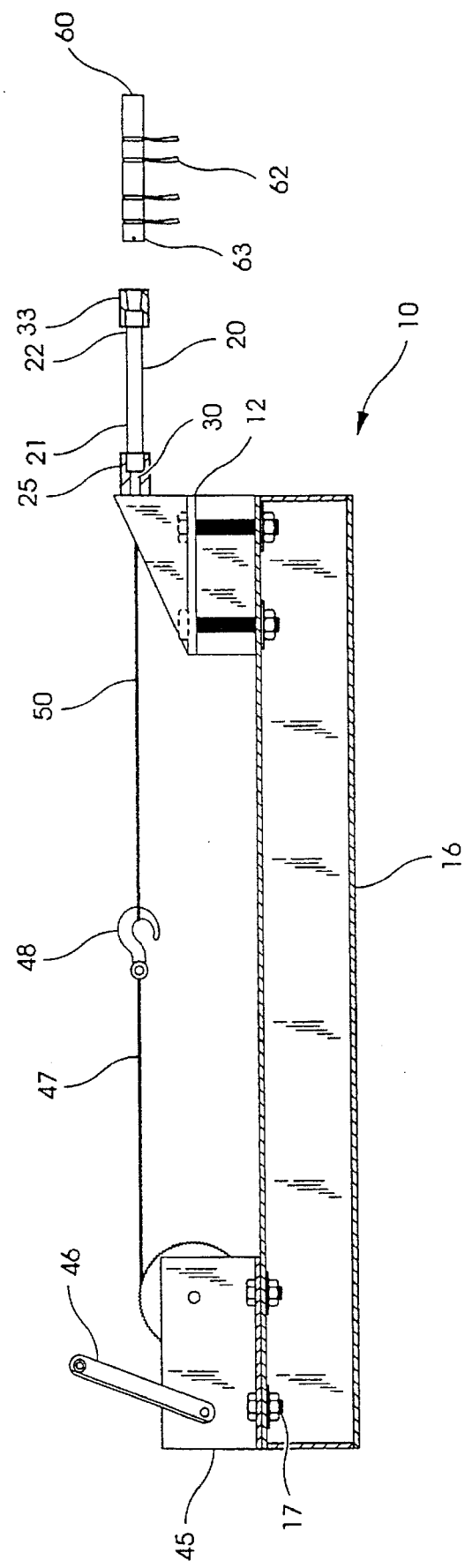
FIG. 2 is a side cross-sectional view of a device connected to a rolled, continuous stationary phase.
Figure 3:
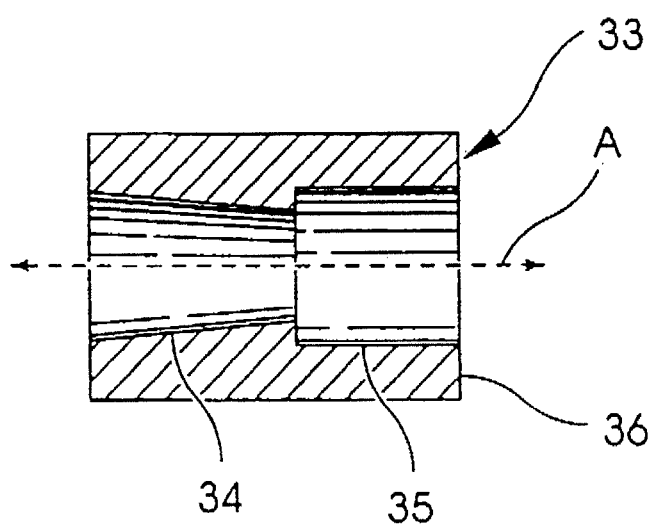
FIG. 3 is a side cross-sectional view of the funnel member used for column packing.

One preferred embodiment of the present invention provides a device 10 for packing chromatography columns such as that depicted in FIGS. 1 and 2. The preferred device 10 includes a brace member 11 having an engagement surface 12 for engaging or supporting an end of a chromatography column 20, a funnel member 33 having converging walls 34 (FIG. 3) at a flare angle configured to radially compress the continuous stationary phase of fabric 60 for entry into the column 20, and a mechanism for applying mechanical force to pull the fabric 60 through the funnel and into the column 20. As used herein, the term flare angle refers to the angle defined between the converging walls 34 and the longitudinal axis "A" (FIG. 3) of the funnel member. The brace member 11 and the means for applying mechanical force are configured to facilitate pulling the phase 60 into the column 20.

The brace member 11 defines a thru-hole 13 at a location such that a passageway 23 defined through the column 20 can be aligned with the thru-hole 13 of the brace member 11 when the end 21 of column 20 is engaged with the engagement surface 12 of the brace member 11. The brace member 11 is preferably composed of a material such as metal or plastic, for example steel, which is strong enough to resist movement or mechanical failure when subjected to the forces necessary to pull the stationary phase into the column 20.

The preferred device also includes a funnel member 33 (FIG. 3) which is engageable with the end 22 of the column 20 which is opposite the end 21 engaged with engagement surface 12. As mentioned previously, the preferred funnel member 33 has converging walls 34, which generally form a conical section and which provide a flare angle configured to radially compress the fabric 60 for entry into the passageway of the column 20 when the fabric 60 is pulled through the funnel member 33 in the direction of convergence of walls 34. Preferably, the column 20 is cylindrical and the diameter of the continuous stationary phase 60 is reduced to a diameter slightly less than the inner diameter (I.D.) of the column 20 as it is radially compressed. The flare angle employed will depend upon the bulk density and other properties, such as tensile strength, of the continuous stationary phase 60, as well as the packing density desired, and can be chosen to facilitate a smooth transition of the phase 60 into the column 20.

The column-engaging end 36 of funnel member 33 preferably has an I.D. slightly greater than the outer diameter (O.D.) of the column 20, so that the column 20 is receivable in the engaging end 36 of the funnel member 33. In this manner, and with the converging walls 34 converging to a diameter essentially equal to the I.D. of column 20, a smooth surface transition between the walls 34 and the interior walls of the column 20 is provided to facilitate passage of the continuous stationary phase 60 into the column 20 while avoiding damage to the phase 60.

In the preferred device 10, the brace member 11 is held in spaced relationship relative to a mechanism for applying mechanical force to pull the rolled continuous stationary phase 60 through the funnel member 33 and into the column 20. The invention contemplates employment of any one of several means for applying mechanical force which are well known in the art. For example, mechanical force can be applied via manual operation of a mechanism which leverages the applied manual force so as to increase the same and direct the increased force to the positioning of the stationary phase 60 into the column 20. In the illustrated embodiment, a hand drawn winch 45 is utilized, although other means such as levers, screw drives or the like can also be used. It is also contemplated that an electric or hydraulically driven motor or winch could also be employed to deliver mechanical force instead of the hand operated winch 45 or other manually-operated means.

Referring to FIGS. 1 and 2, a hand drawn winch 45 and a cord member 44 are operable to pull the rolled continuous stationary phase 60 through the funnel member 33 and into the passageway of column 20. In one embodiment the winch 45 and brace member 11 (optionally with appropriate spacers such as 11A) are bolted to a base 16 by mounting bolts 17. The cord member 44 preferably includes a cable 47 having a first end engaged to the winch 45 and a second end 49 engaged to wire 50 which is threadable through the thru-hole 13 of the brace member, the passageway of a column 20, and the funnel member 33. The wire 50 is attachable to the continuous stationary phase 60. A connecting device, such as a look 48, is attached to the second end 49 of the cable 47 for connecting to the wire 50. The cable 47 can be constructed from any suitable material having high tensile strength and resisting elongation under the forces applied, for example a metal such as stainless steel, or a polymeric material such as Kevlar® aromatic polyamide.

According to a preferred embodiment, the device 10 for packing continuous stationary phases also includes a stopper member 25 having a bore 30 therethrough. The stopper member 25 aids in aligning the passageway 23 of the column 20 with the thru-hole 13 in the brace member 11 and therefore aligns the continuous stationary phase 60 with the directional pull of the winch 45. Such alignment minimizes shearing of or other damage to the continuous stationary phase 60 as it is positioned into the column 20.

Figure 4:
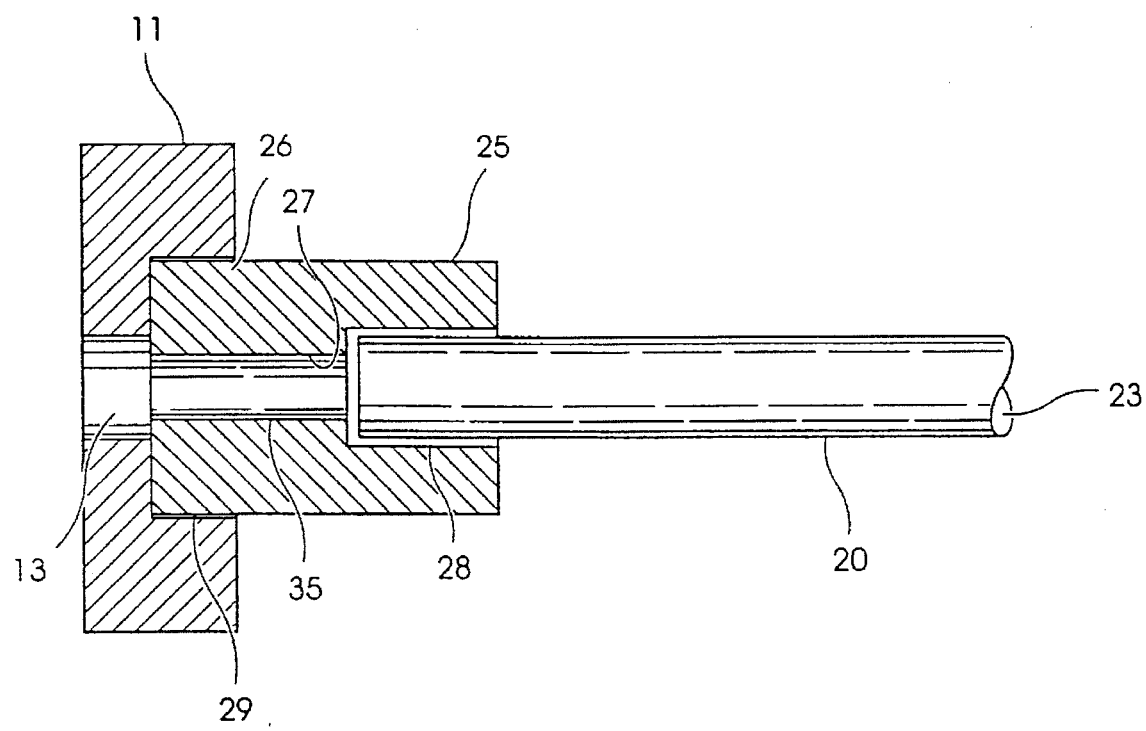
FIG. 4 is a side cross-sectional view of a brace member, stopper, and column.

Referring now to FIG. 4, the stopper member 25 preferably has a first bore 27 having an I.D. equivalent to the I.D. of column 20 and a second bore 28 having an I.D. slightly greater than the O.D. of column 20 so that column 20 is receivable in the second bore 28 of the stopper member 25. This permits entry of the column 20 into the stopper member 25 to abut interior walls defined at the transition between the first and second bores 27 and 28, as illustrated. In the preferred embodiment, the stopper member 25 is a separate unit. In this manner, the packing of columns of differing outside diameters can be facilitated by selecting and employing a stopper member 25 having the appropriate dimensions.

In the preferred device, the first end 29 of the stopper member 25 contacts the engagement surface 12 of the brace member 11 at a location such that the passageway 23 of column 20 is aligned and in communication with the thru-hole 13 of the brace member 11 when an end of column 20 is inserted in the bore 30 of the stopper member 25. In this arrangement employing the stopper member 25, column 20 is of course ultimately engaged to the engagement surface via the stopper member 25.

The engagement surface 12 of the brace member 11 is preferably adapted to secure the stopper member 25 in place when the two components are engaged with one another. For example, flanges or similar proturbances can be provided in a spaced relationship around the thru-hole 13 of a brace member 11, and configured to secure the stopper member 25 in position against the engagement surface 12. Preferably, though, a recess is defined in the engagement surface 12 about the thru-hole 13, the recess being dimensioned to receive the end of the stopper member 25 as illustrated (FIG. 4).

The stopper member 25 and funnel member 33 can be machined or otherwise formed from suitable metal (e.g. stainless steel or aluminum) stock or from standard chromatography column end-fittings which correspond to the O.D. of a column of interest, for example ⅜", ½", etc. For example, such fittings are commercially available under the brand name Valco®.

The column 20 may be composed of any suitable material known in the art such as glass or stainless steel (e.g. 316) seamless tubing. Because of the extreme tensile force and friction between the column 20 walls and the stationary phase 60 during packing, it is preferable to remove snags, burrs, or other anomolies present inside or at the ends of the columns 20 prior to the packing procedure. The columns 20 can be polished at both ends using a high speed lathe. Columns 20 are also preferably conditioned against corrosion by pacifying the inner surfaces by treatment with an acidic solution such as concentrated nitric acid, for example for a period of 30 minutes, followed by rinsing with water. Additionally, prior to packing, the interior of columns 20 are preferably with an appropriate lubricant, for example polyethylene glycol, M.W. 200 (PEG 200) to reduce friction during the packing operation.

To condition the stationary phase 60 for attachment to wire 50, it is preferably pierced at one end with, for example, an awl or a relatively small, e.g. ¹⁄₁₆", high speed drill. The pierced hole 63 is then threaded with a length of wire 50. The wire 50 preferably has a small diameter and high tensile strength. The preferred material is Kevlar® aromatic polyamide fiber, which is non-abrasive and has a greater resistance of elongation than steel. A loop or loops of wire 50 are then threaded through the funnel, column 20, stopper member 25 and then the thru-hole 13 of brace member 11. The loop or loops are then secured to the hook 48 or other connecting device.

The continuous stationary phase 60 is preferably lubricated before being packing into the column 20. The lubricant can be chosen from lubricants well known in the art, for example, polyethyleneglycol such as PEG 200.

Figure 5A:
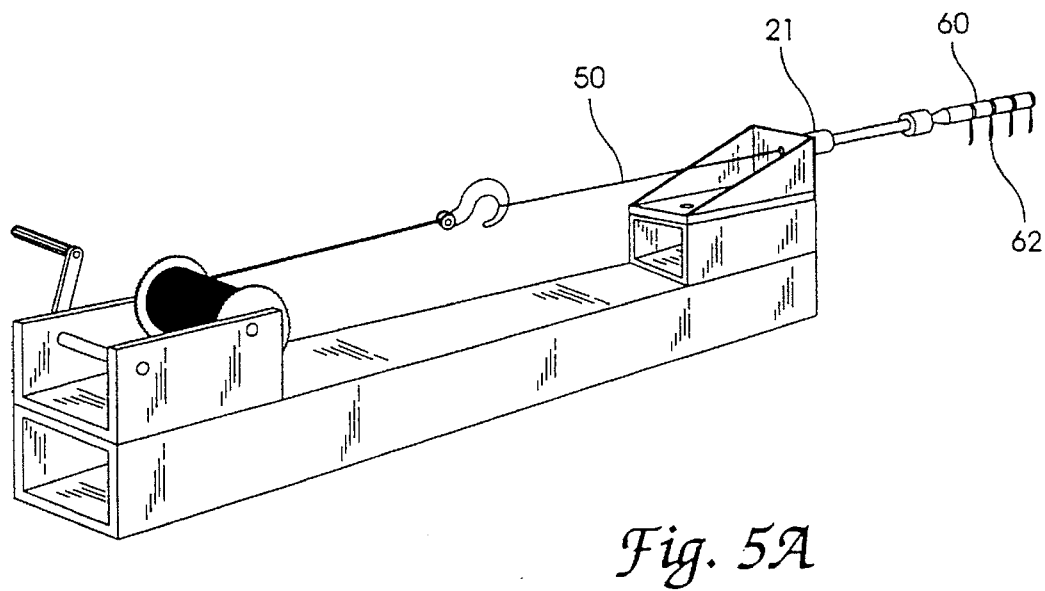
FIGS. 5 (A)–(C) show the progression of rolled stationary phase into a column according to the invention.
Figure 5B:
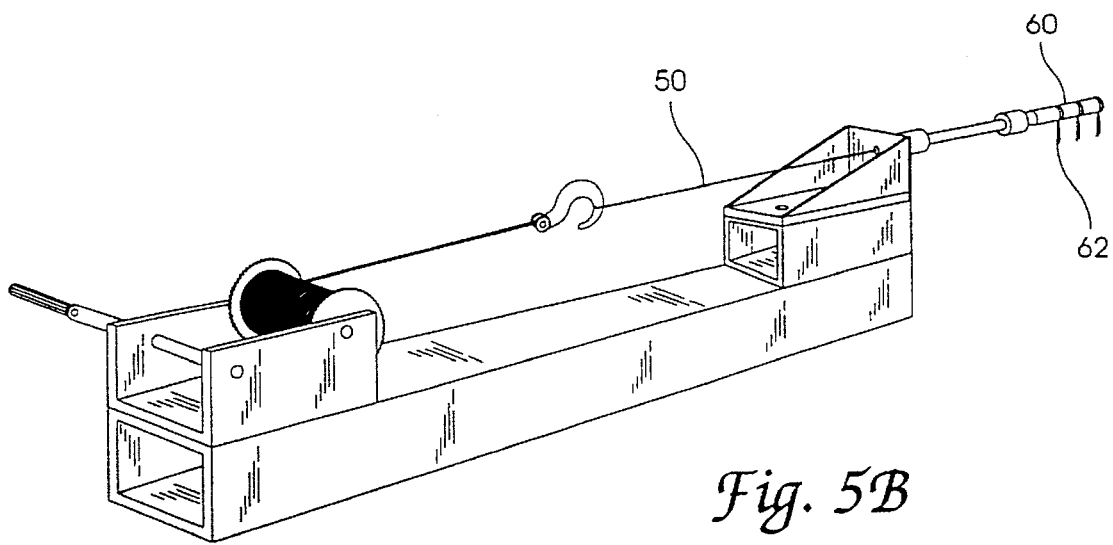
Figure 5C:
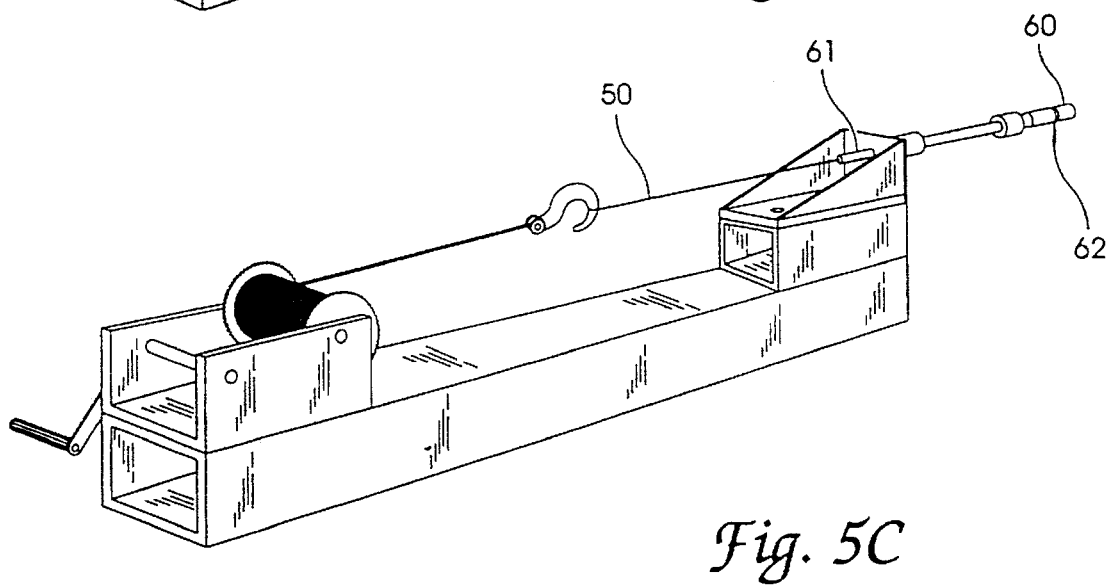
Figure 6A:
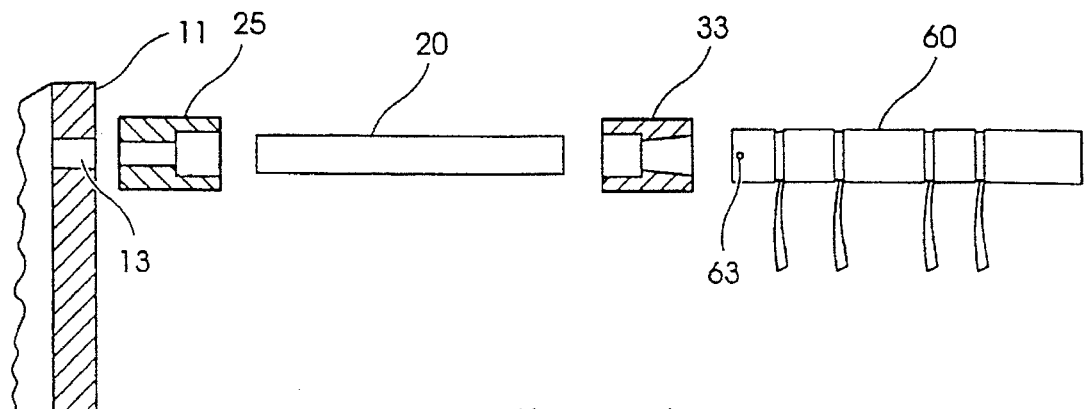
FIGS. 6 (A)–(C) show side cross-sectional views of the column, stopper, and funnel assembly during a packing sequence.
Figure 6B:
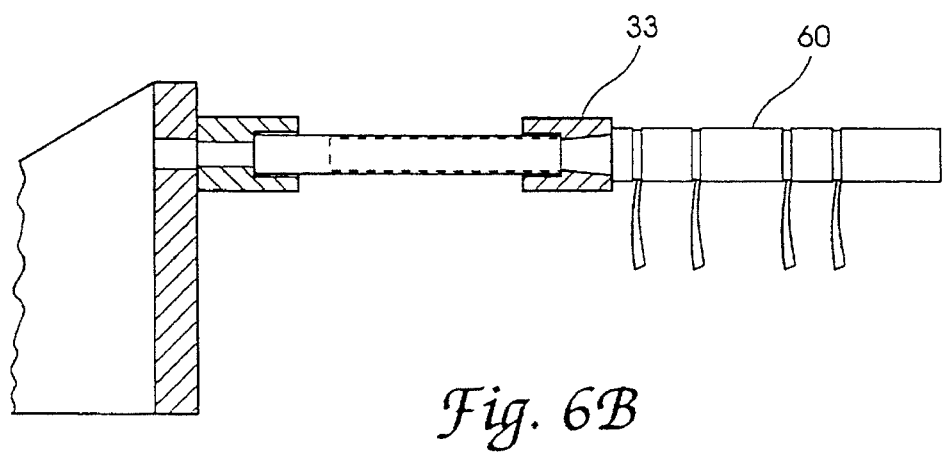
Figure 6C:
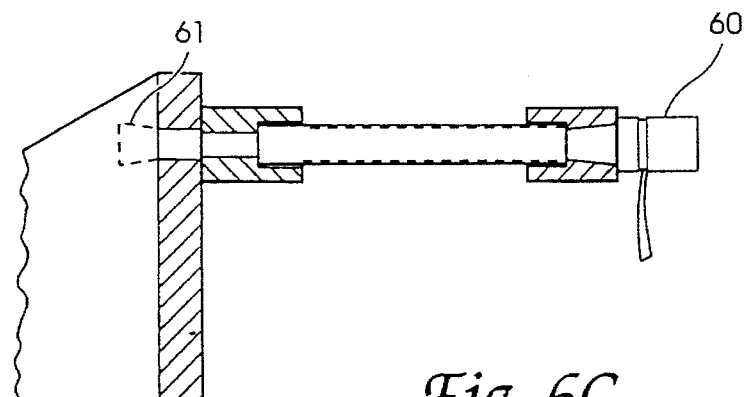

Referring to FIGS. 5 and 6, shown are drawings which further illustrate the packing operation. An engaging end 36 of the funnel member 33 is engaged to the column 20 and the column 20 is engaged to the engagement surface 12 of the brace member 11. As previously described, in the preferred operation, the column 20 is engaged to the surface 12 via stopper member 25. The wire 50, threaded through the other components and attached to the stationary phase 60 as discussed above, is also connected to the hook 48. In turn, the hook 48 is connected to the cable 47 and thus ultimately to the winch 45. Rotating the handle 46 to operate the winch 45 pulls the stationary phase 60 through funnel member 33 and into and through the column 20. This packing operation is preferably executed by applying a slow, steady force on the phase 60 as it proceeds through the funnel member 33 and the column 20. As well, it is preferred to slightly twist the stationary phase 60 in the direction it was rolled to facilitate the packing procedure. In addition, it is preferred that the stationary phase 60 be secured for handling using plastic ties 62 or other securing means (such as Velcro® hook and loop fastener strips) positioned along the entire length of the phase 60. The ties 62 can be removed, e.g. cut off, as they near the column 20 as the phase 60 is pulled into and through the column 20.

The stationary phase 60 is preferably pulled through the column 20 so that a portion of the phase 60 can be observed protruding through the through hole 13. It is desirable that the portion of stationary phase 60 containing the hole 63 clear the end of the column 20 so that it can be removed. Once the rolled fabric 60 is pulled through the column 20, the device 10 is relieved of tension and the stopper member 25 and funnel member 33 can be removed. The column can then be finished by cutting the continuous stationary phase 60 flush with the end of the column 20 using a sharp instrument such as a razor blade. An appropriate standard liquid chromatography column end-fitting can then be fitted to the column 20. Any lubricant utilized in the packing operation can be washed from the stationary phase with an appropriate eluent after completion of the packing operation.

If the rolled stationary phase 60, must be later removed from the column 20, a punch with an O.D. corresponding to the I.D. of a column 20 can be used. Alternatively, the packed column can be pumped full of lubricant such as PEG 200, and the stationary phase pushed or pumped from the column. This enables the valuable stationary phase 60 to be retrieved with minimal damage.

In a preferred aspect of the invention, the continuous stationary phase 60 can be a sheet of continuous stationary phase material rolled into a cylindrical configuration. It is contemplated that this rolling step may be manual or automated. Materials for the continuous stationary phase can be chosen from various types of materials which are within the ambit of the skilled artisan. Preferably, the stationary phase is formed from a rectangular or square sheet of fabric. Rectangular fabric can be oriented in a warp parallel, fill parallel or bias direction. The length of the fabric in the direction of flow within the column will be selected depending on the desired length of the column. The width and thickness of the fabric will, at least in part, determine the diameter of the roll of fabric and hence the extent of radial compression necessary to position the material in a given column diameter. Preferred stationary phases are prepared as described in a copending U.S. patent application of Michael Ladisch et al. entitled NOVEL METHOD FOR DERIVATIZATION OF CELLULOSE STATIONARY PHASES, filed Jun. 15, 1994, which is hereby incorporated herein by reference in its entirety.

The stationary phase is preferably rolled to a cylindrical configuration on a flat, hard and smooth surface, beginning with the smallest uniform fold possible. The fabric is rolled by hand, or by a mechanical device so that the entire length of the fabric, the length to be perpendicular to flow, is in a cylindrical configuration. The tightness of the roll can be increased by repeatedly rolling the stationary phase across a table or other suitable surface using the palms of the hands, while exerting an increasingly stronger downward force on the roll. Once sufficient tightness or compaction of the roll has been achieved, the roll can be secured for handling using plastic ties 62 or other securing means as described above.

Preferred columns prepared in accordance with the invention, containing rolled cotton or a similar rolled cellulosic fabric, can have advantageous void fractions and packing densities. For example, advantageously high packing densities of greater than about 0.5 grams/cc can be achieved in the column, typically falling within the range of about 0.5 g/cc to about 0.6 g/cc. Advantageously low void fractions of about 0.4 or less, or even about 0.3 or less (as measured by bovine serum albumin, BSA), can also be readily achieved in accordance with the invention. Columns of the invention exhibit advantageously low pressure drops and stability against mechanical breakdown as demonstrated by the observance of consistent pressure drops over extended periods of use. As well, columns prepared in accordance with the invention have advantageous flow properties, for example readily providing linear flow velocities in excess of 50 cm/min and ranging up to about 100 cm/min.

Moreover, using rolled fabric stationary phases in the invention provides the beneficial ability to pack large quantities of fabric into columns in a manner giving the high density desired while avoiding more laborious methods such as those which would require the cutting, stacking and packing of discs of fabric. Moreover, the use of stacked discs and attendent cutting operations will invariably lead to significant amounts of waste stationary phase and thus overall increases in production costs. As well, physical limitations in effectively and reproduceably stacking discs, such as those leading to limitations in column height, may be avoided in accordance with the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for packing a liquid chromatography column with a rolled fabric stationary phase, comprising:
    a brace member having an engagement surface, the brace member defining a thru-hole at a location so that a passageway defined through the column is aligned with the thru-hole of the brace member when a first end of the column is engaged with the engagement surface of the brace member;
    a funnel member engageable with an end of the column opposite the first end, the funnel member having converging walls configured to radially compress the rolled fabric stationary phase for entry into the passageway of the column when the rolled fabric stationary phase is pulled through the funnel member;
    a mechanism for pulling the stationary phase through the funnel member;
    a cord member attached to the mechanism, the cord member being threadable through the thru-hole, the passageway and the funnel member and attachable to the rolled fabric stationary phase; and
    the mechanism and the cord member operable to pull the rolled fabric stationary phase through the funnel member wherein the stationary phase is radially compressed, and into the passageway of the column.

2. The device of claim 1 wherein:
    the mechanism comprises a winch held in spaced relationship to the brace member.

3. The device of claim 2 wherein the cord member comprises aromatic polyamide fiber.

4. The device of claim 1 further comprising a stopper member defining a bore therethrough, wherein the column is receivable in the bore of the stopper member, and the stopper member is engagable with the engagement surface of the brace member at a location so that the passageway in the column is in communication with the thru-hole of the brace member when an end of the column is received in the bore of the stopper.

5. The device of claim 4 wherein the engagement surface of the brace member comprises flanges spaced around the thru-hole of the brace member, the flanges being configured to secure the location of the stopper member when engaged with the engagement surface.

6. The device of claim 4 wherein the engagement surface includes a recess about the thru-hole, the recess dimensioned to receive and fix the location of the stopper when engaged with the engagement surface.

7. The device of claim 4 wherein:
    the thru-hole of the brace member is aligned with a directional pull of the winch; and
    the stopper member is configured to align a longitudinal axis of the column with the thru-hole of the brace and thus also with the directional pull of the winch.

8. The device of claim 1 wherein the funnel member is engageable to the column at an engaging end of the funnel member, the engaging end being dimensioned to receive an end of the column.

9. The device of claim 1 wherein the engaging end of the funnel member is cylindrical in shape and has an inner diameter sized to receive a cyclindrical column.

* * * * *

UNITED STATES PATENT AND TRADEMARK OFFICE
CERTIFICATE OF CORRECTION

PATENT NO. : 5,624,553
DATED : April 29, 1997
INVENTOR(S) : Michael Ladisch, et. al.

It is certified that error appears in the above-identified patent and that said Letters Patent is hereby corrected as shown below:

In col. 4, line 27, please delete "look" and insert in lieu thereof --hook--.

Signed and Sealed this

Second Day of June, 1998

Attest:

BRUCE LEHMAN

*Attesting Officer*     *Commissioner of Patents and Trademarks*